United States Patent
Nolan et al.

(10) Patent No.: US 7,153,656 B2
(45) Date of Patent: Dec. 26, 2006

(54) NUCLEIC ACID SEQUENCE DETECTION USING MULTIPLEXED OLIGONUCLEOTIDE PCR

(75) Inventors: John P. Nolan, Santa Fe, NM (US); P. Scott White, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 294 days.

(21) Appl. No.: 10/336,266

(22) Filed: Jan. 3, 2003

(65) Prior Publication Data

US 2004/0091879 A1      May 13, 2004

(51) Int. Cl.
*C12Q 1/68*      (2006.01)
*C12P 19/34*     (2006.01)
*C07H 21/02*     (2006.01)
*C07H 21/04*     (2006.01)

(52) U.S. Cl. .................. 435/6; 435/91.2; 536/23.1; 536/24.3

(58) Field of Classification Search .............. 435/6, 435/91.2; 536/23.1, 24.3
See application file for complete search history.

(56) References Cited

U.S. PATENT DOCUMENTS

| | | | |
|---|---|---|---|
| 4,770,992 A | 9/1988 | VandenEngh et al. | 435/6 |
| 4,988,617 A | 1/1991 | Landegren et al. | 435/6 |
| 5,629,158 A | 5/1997 | Uhlen | 435/6 |
| 5,639,611 A * | 6/1997 | Wallace et al. | 435/6 |
| 5,679,524 A | 10/1997 | Nikiforov et al. | 435/6 |
| 5,736,330 A | 4/1998 | Fulton | 435/6 |
| 5,876,924 A | 3/1999 | Zhang et al. | 435/5 |
| 5,912,148 A | 6/1999 | Eggerding | 435/91.2 |
| 6,027,889 A * | 2/2000 | Barany et al. | 435/6 |
| 6,235,889 B1 | 5/2001 | Ulanovsky | 536/24.3 |
| 6,238,868 B1 | 5/2001 | Carrino et al. | 435/6 |
| 6,287,766 B1 * | 9/2001 | Nolan et al. | 435/6 |
| 6,312,892 B1 * | 11/2001 | Barany et al. | 435/6 |
| 6,361,944 B1 * | 3/2002 | Mirkin et al. | 435/6 |

OTHER PUBLICATIONS

PCT/US99/13928 (Weiner) filed Jun. 22, 1999.
EP1131113 (Schouten) filed May 9, 2001.
Pastinen et al., 1997, Genome Research 7: 606.
Tobe et al., 1996, Nucleic Acids Res. 24: 3728.
Favis et al, 2000, Nature Biotech. 18: 561.
Landegren et al., 1988, Science 241: 1077 and.
Ugozzoli et a., 1992, GATA 9(4): 107.
U.S. Appl. No. 09/877,819, filed Jun. 7, 2001.

\* cited by examiner

*Primary Examiner*—Ethan Whisenant
(74) *Attorney, Agent, or Firm*—Kenneth K. Sharples; Ray G. Wilson

(57) ABSTRACT

Methods for rapidly detecting single or multiple sequence alleles in a sample nucleic acid are described. Provided are all of the oligonucleotide pairs capable of annealing specifically to a target allele and discriminating among possible sequences thereof, and ligating to each other to form an oligonucleotide complex when a particular sequence feature is present (or, alternatively, absent) in the sample nucleic acid. The design of each oligonucleotide pair permits the subsequent high-level PCR amplification of a specific amplicon when the oligonucleotide complex is formed, but not when the oligonucleotide complex is not formed. The presence or absence of the specific amplicon is used to detect the allele. Detection of the specific amplicon may be achieved using a variety of methods well known in the art, including without limitation, oligonucleotide capture onto DNA chips or microarrays, oligonucleotide capture onto beads or microspheres, electrophoresis, and mass spectrometry. Various labels and address-capture tags may be employed in the amplicon detection step of multiplexed assays, as further described herein.

5 Claims, 6 Drawing Sheets

Capture MOLigos onto microspheres containing ATS (complements of CTS) and then read fluorescence on flow cytometer. Many sets of MOLigos can type many polymorphisms simultaneously in solution, and each captured onto a different microsphere with a unique address tag in a multiplexed set to be read simultaneously.

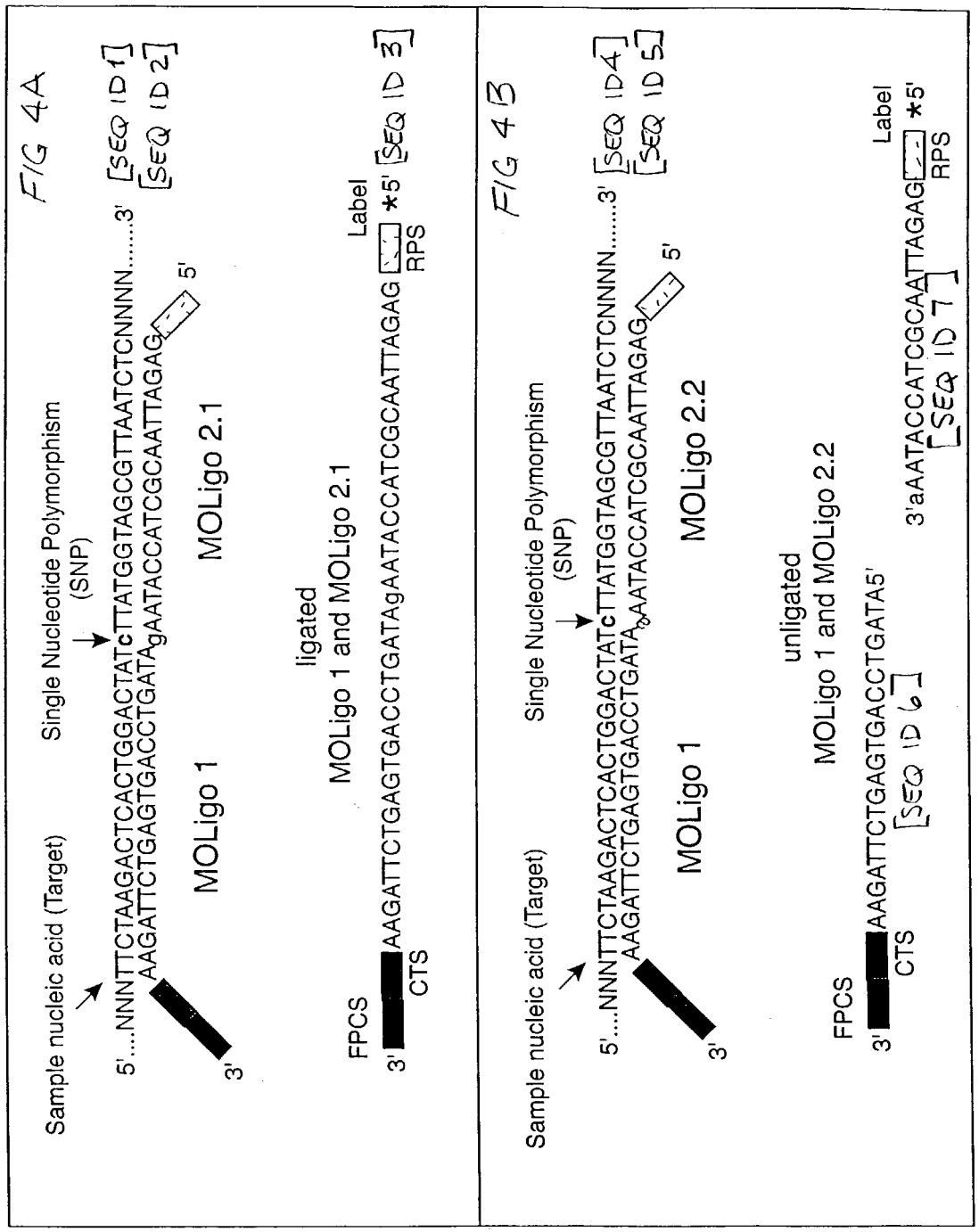

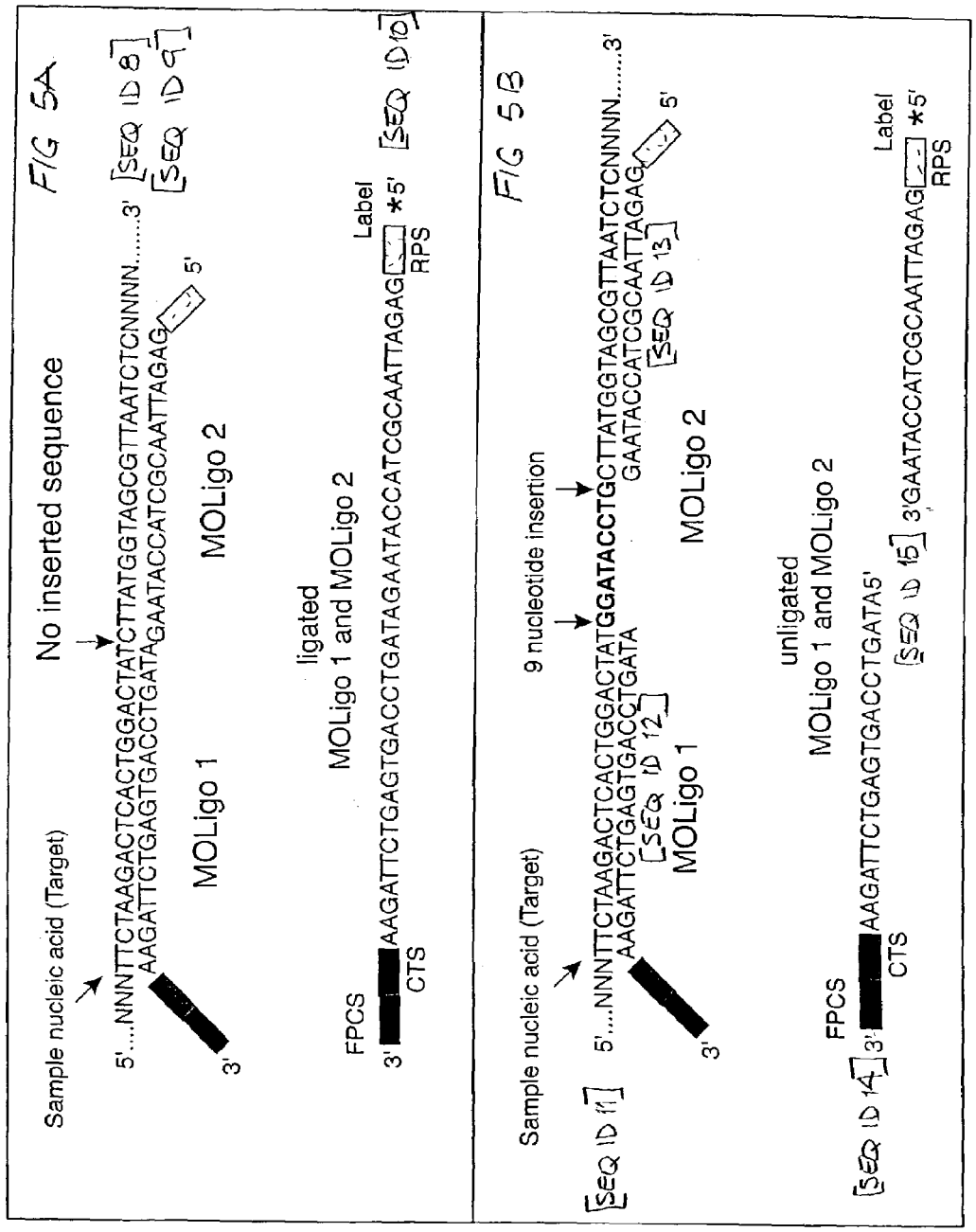

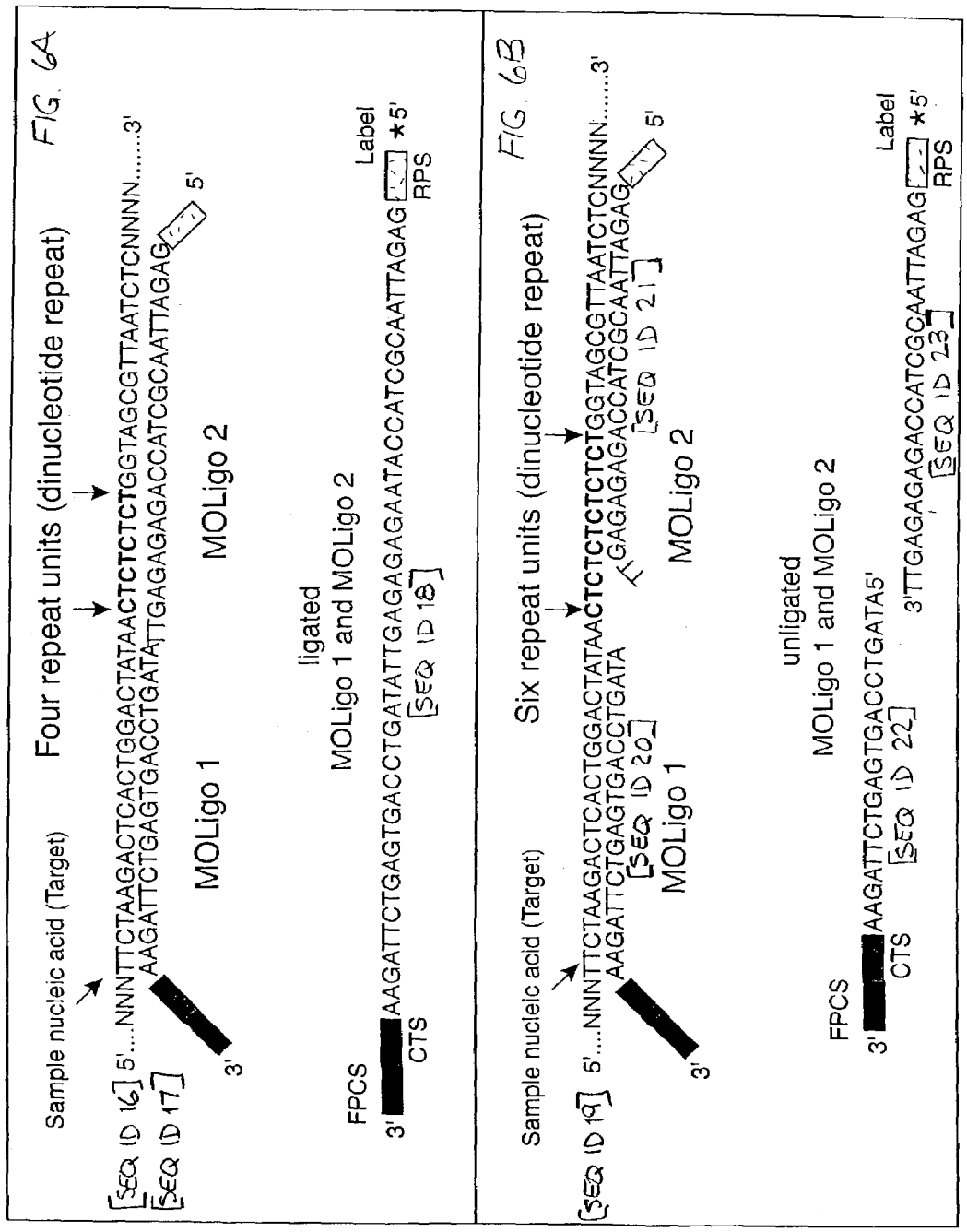

NUCLEIC ACID SEQUENCE DETECTION USING MULTIPLEXED OLIGONUCLEOTIDE PCR

STATEMENT REGARDING GOVERNMENT RIGHTS

This invention was made with government support under Contract No. W-7405-ENG-36 awarded by the U.S. Department of Energy to The Regents of The University of California. The government has certain rights in this invention.

RELATED CASES

The present patent application claims priority from Provisional Patent Application No. 60/063,685, which was filed on Oct. 28, 1997, Nonprovisional Patent Application Ser. No. 09/182,869, issued as U.S. Pat. No. 6,287,766 on Sep. 11, 2001, and Nonprovisional Patent Application Ser. No. 09/953,534, filed Sep. 11, 2001, all incorporated herein by reference for all purposes.

FIELD OF THE INVENTION

The present invention relates generally to methods for the rapid identification of specific nucleic acid sequences in sample polynucleotides using sets of modular oligonucleotides and PCR amplification in single or multiplexed formats, optionally using flow cytometry for detection. The methods of the invention are useful for the identification of specific nucleic acid sequence alleles, such as single nucleotide polymorphisms, insertions, deletions, inversions, repeats, and other sequence features. The multiplexing feature of the invention enables high throughput identification of multiple alleles simultaneously.

BACKGROUND OF THE INVENTION

The determination of the DNA base sequence of the human genome will have a major impact on biomedical science in the next century. The completion of the first complete human DNA enhances a range of applications from genetic mapping of disease-associated genes to diagnostic tests for disease susceptibility and drug response. The detection of the base composition at specific, variable DNA sites, such as single nucleotide polymorphisms (SNPs), insertion/deletion events, repeats, and the like, is especially important. The current generation of sequence detection methods are too slow and costly to meet large-scale DNA analysis requirements. Thus, there is a need for faster, more efficient methods for detecting specific genetic sequences, for example SNPs and other variable sites, i.e., for "scoring" the actual base identities at specific sites.

SNPs have a number of uses in mapping, disease gene identification, and diagnostic assays. All of these applications involve the determination of the specific base composition at the SNP site. Detection strategies for biological agents will increasingly make use of sequence information. Conventional sequencing can provide this information, but is impractical for screening a large number of sites in a large number of individuals. Several alternative methods have been developed to increase throughput.

Two techniques have been developed to determine base composition at a single site: minisequencing (See, e.g., "Minisequencing: A Specific Tool For DNA Analysis And Diagnostics On Oligonucleotide Arrays," by Tomi Pastinen et al., Genome Research 7, 606 (1997)), and oligo-ligation (See, e.g., "Single-Well Genotyping Of Diallelic Sequence Variations By A Two-Color ELISA-Based Oligonucleotide Ligation Assay," by Vincent O. Tobe et al., Nucleic Acids Res. 24, 3728 (1996)). In minisequencing, an oligonucleotide primer is designed to interrogate a specific site on a sample template, and polymerase is used to extend the primer with a labeled dideoxynucleotide. In oligo-ligation, a similar oligonucleotide primer is designed, and ligase is used to covalently attach a downstream oligo that is variable at the site of interest. In each case, the preference of an enzyme for correctly base-paired substrates is used to discriminate the base identity that is revealed by the covalent attachment of a label to the oligonucleotide. In most applications these assays are configured with the oligonucleotide immobilized on a solid substrate, including microplates, magnetic beads and recently, oligonucleotides microarrayed on microscope slides. Detection strategies known to those skilled in the art include direct labeling with fluorescence detection or indirect labeling using biotin and a labeled streptavidin with fluorescent, chemiluminescent, or absorbance detection.

Oligonucleotide microarrays or "DNA chips" have generated much attention for their potential for massively parallel analysis. The prospect of sequencing tens of thousands of bases of a small sample in just a few minutes is exciting. At present, this technology has limited availability because arrays to sequence only a handful of genes are currently available, with substantial hardware and consumable costs. In addition, the general approach of sequencing by hybridization is not particularly robust, with the requirement of significant sequence-dependent optimization of hybridization conditions. Nonetheless, the parallelism of an "array" technology is very powerful, and multiplexed sequence determination is an important element of the new flow cytometry method.

U.S. Pat. No. 6,287,766, issued Sep. 11, 2001, and incorporated herein by reference, teaches minisequencing by flow cytometry, a technology that has the potential to meet the current and future demands for low cost, high throughput assays for genetic variation assessment. However, because it is so efficient, the technology creates its own limiting problem, which is a severe bottleneck upstream of the assay. The bottleneck is created by the need to amplify by polymerase chain reaction (PCR) individual DNA fragments that contain nucleotide regions or sites known to be variable among individuals. Other current technologies have severe limitations that make an upstream bottleneck not as noticeable, but will eventually limit all large-scale efforts that are simply a more parallel approach of less efficient strategies.

Most SNP scoring (i.e., identification) technologies are "one at a time" assays that are performed either as parallel, singleplex assays (such as the oligo-ligation assay in 96 or 384 wells of a microtiter plate) or are single-to-moderately parallel assays with high serial throughput (e.g., mass spectrometry platform). Technologies that would permit scoring SNPs located at many different sites simultaneously (high throughput of multiplex) are needed to meet current and projected throughput and cost requirements. The flow cytometry platform of the '766 patent has such potential, and represents a substantial increase toward meeting these throughput needs.

For example, a SNP scoring project that will score 100 SNPs on 96 individuals would require two runs of a 50-plex minisequencing assay for each individual. At the slowest rates of the assay, this requires approximately 3 to 6 hours to perform. In contrast, the PCR amplification of the individual fragments containing the sites to be scored would require 100 separate PCR reactions per individual, followed by a pooling of these products for the scoring assay. The amplification steps alone would occupy one 96-well PCR machine for over 200 hours. Assuming around-the-clock operation to change out the samples every two hours, more than 8 days of operation of a PCR machine would be needed to feed the flow cytometer for 3 to 6 hours.

This disparity will become even more apparent as larger multiplexed microsphere bead sets become available; 100 bead sets are currently commercially available, while an alternative labeling strategy (Q-dots) that projects over 1 million beads within a multiplexed set should be available within 1–2 years, or sooner. Such bead sets allow individual beads to be uniquely identified. Clearly a better means of providing template DNA for these assays or a better assay needs to be developed. As mentioned previously, the PCR bottleneck is common to nearly all SNP scoring technologies, but other technologies do not have the throughput of the flow cytometry platform that would make this a practical limitation. Accordingly, there is a need to eliminate or improve the throughput of processes upstream of the flow cytometry platform.

Among the many SNP scoring technologies, the only one with the sensitivity to use unamplified, genomic DNA as the substrate is the Invader assay (Third Wave Technologies, Madison, Wis.). This technology uses a two-stage signal amplification strategy that provides a level of sensitivity that allows for analyses to be performed on genomic DNA without PCR amplification of the region around the SNP. Unfortunately, the ability to multiplex the Invader assay is limited to only a few SNPs per assay. In addition, Invader assays are currently technically difficult, and require careful design of oligonucleotides to insure that multiple assays all occur optimally at the same temperature. These constraints severely limit the use of Invader assays in high throughput drug discovery strategies and have not gained widespread use. Another technology, the TaqMan assay (PE ABI, Foster City Calif.) allows simultaneous PCR amplification and SNP scoring in real time (kinetic PCR, as opposed to end-point detection). Unfortunately, as with the Invader assay, the ability to multiplex TaqMan assays is limited to only a few sites, and is typically only performed on single SNPs or other targets. None of the existing technologies has the throughput capacity that makes the PCR bottleneck as evident as the flow cytometry-based SNP assays of the '766 patent.

U.S. Pat. No. 4,988,617, issued January 1991 to Landegren et al. ("Landegren"), and incorporated herein by reference, describes a method for determining a nucleic acid sequence in a region with a known polymorphism. This method comprises the steps of performing oligonucleotide ligation with one labeled and one tagged oligonucleotide, followed by capture onto a solid support. This solid support can be a membrane (e.g., nitrocellulose or nylon), or a well of a microtiter plate, or a microsphere. Landegren et al. propose that PCR amplification of the target DNA be done prior to annealing the probe elements to the target sequence.

Various advantages, and novel features of the invention will be set forth in part in the description which follows, and in part will become apparent to those skilled in the art upon examinations of the following or may be learned by practice of the invention. The objects and advantages of the invention may be realized and attained by means of the instrumentalities and combinations particularly pointed out in the appended claims.

SUMMARY OF THE INVENTION

The present invention provides methods for rapidly detecting single or multiple sequence alleles in a sample nucleic acid. The methods of the invention may be used to identify the presence or absence of specific nucleotide sequences in a sample nucleic acid, including without limitation, detecting single nucleotide polymorphisms (SNPs), detecting the presence or absence of a particular nucleotide sequence useful in the identification of a particular organism or a particular genotype thereof, and in the detection of sequence insertions, deletions, inversions and repeated sequences. The methods of the invention may also be used for qualitative analysis of various genetic states, such as the exact nucleotide base identity in a particular SNP.

The methods of the invention utilize a novel approach for detecting a target sequence, wherein sequence discrimination occurs before nucleic acid is amplified for detection. More specifically, the methods of the invention utilize oligonucleotide pairs capable of annealing specifically to a target allele and discriminating among possible sequences thereof, and in the presence of ligase, ligating to each other to form an oligonucleotide complex when a particular sequence feature is present (or, alternatively, absent) in the sample nucleic acid. The design of each oligonucleotide pair permits the subsequent high-level PCR amplification of a specific amplicon when the oligonucleotide complex is formed, but not when the oligonucleotide complex is not formed. The presence or absence of the specific amplicon is used to detect the allele. Detection of the specific amplicon may be achieved using a variety of methods well known in the art, including without limitation, oligonucleotide capture onto DNA chips or microarrays, oligonucleotide capture onto beads or microspheres, electrophoresis, and mass spectrometry. Various labels and address-capture tags may be employed in the amplicon detection step of multiplexed assays, as further described herein.

Multiple alleles in a sample nucleic acid may be simultaneously detected using a multiplex of oligonucleotide pairs, wherein each oligonucleotide pair is specific for a particular target allele, but all pairs share common primer sequences or primer sequence sites, thereby enabling the simultaneous PCR amplification of a series of amplicons corresponding to a series of alleles after oligonucleotide hybridization to target alleles and formation of ligated complexes (or not).

In one embodiment of the method, the presence of a specific nucleotide sequence in a sample nucleic acid is identified by hybridizing a pair of oligonucleotides thereto, which oligonucleotides are capable of ligating together when hybridized to the sample nucleic acid if the specific nucleotide sequence is present therein. More specifically, the two oligonucleotides in the pair comprise sequences which in tandem are complementary to a contiguous sequence of the sample nucleic acid spanning or including the specific nucleotide sequence. In the presence of ligase, the two oligonucleotides will ligate to form an oligonucleotide complex when the specific nucleotide sequence is present, but not when the specific sequence is absent in the sample. One oligonucleotide further comprises a tail sequence containing a first PCR primer sequence and the other oligonucleotide further comprises a tail sequence containing the complement of a second PCR primer sequence. The oligonucleotides are then PCR amplified using the first and second PCR primers, and the presence of the specific nucleotide sequence is identified by detecting an amplicon corresponding to a ligated oligonucleotide complex.

In a particular application, the method provides for detecting an allele of a known single nucleotide polymorphism (SNP) in a sample nucleic acid, wherein the allele is defined by the presence of one to four possible nucleotides at a specific site. The nucleotide identity at a SNP site is determined by first hybridizing to the sample nucleic acid one or more oligonucleotide pairs, wherein (i) one or more pairs are capable of ligating together when hybridized to the sample nucleic acid if one of the nucleotides possible at the SNP site is present therein, (ii) each oligonucleotide pair having a means for distinguishing each from the other, and (iii) one oligonucleotide in each pair further comprises a tail sequence containing a first PCR primer sequence and the other oligonucleotide in each pair further comprises a tail sequence containing the complement of a second PCR primer sequence. The oligonucleotides are then PCR amplified with the first and second PCR primers. The identity of the nucleotide at the polymorphism site is determined by detecting the presence or absence of an amplicon corresponding to a ligated oligonucleotide complex, the means for distinguishing amplicons being used to assign a specific nucleotide.

The number of oligonucleotide pairs utilized will depend upon the number of possible nucleotides at the SNP site. In a bi-allelic SNP, at least one, and preferably two oligonucleotide pairs are used. One oligonucleotide pair capable of recognizing one of the two possibilities may be sufficient to determine the identity of the nucleotide at the SNP site. The use of a second oligonucleotide pair, designed to recognize the other possible nucleotide at the SNP site, or additionally to detect the complementary strand will provide redundancy in allele discrimination. One or more additional oligonucleotide pairs, targeted to a nucleotide which is not possible at the SNP site, may be added to provide negative control. In tri-allelic and tetra-allelic discrimination applications, three and four oligonucleotide pairs may be utilized, respectively, but may not be required in all applications.

SNP discrimination using the method of the invention may be conducted in single or multiple reactions. For example, in a bi-allelic SNP discrimination, two oligonucleotide pairs targeted to two different nucleotides at the SNP site may be hybridized to sample and PCR amplified in separate reactions, in which case, incorporating a means for distinguishing the two oligonucleotide pairs is not necessary.

Alternatively, the oligonucleotide pairs may be hybridized to sample and PCR amplified in a single reaction, in which case a means of distinguishing amplicons resulting from PCR amplication of different ligated oligonucleotide pairs, or complexes, is required. Incorporation of a means for distinguishing oligonucleotide pairs enables the identification of amplicons corresponding to ligated oligonucleotides carrying different SNP bases. Means for differentiating oligonucleotides (and thus amplicons) include without limitation, variable sizes, sequence compositions, labels and other sequence features or tags. In one application, a unique polynucleotide capture tag sequence is incorporated into one of the oligonucleotides in a given pair. In this application, PCR amplification generates amplicons carrying the capture tag sequences, which amplicons are therefore capable of hybridizing to a complementary polynucleotide address tag, which may be linked to a solid support or particle for easy detection. For example, the address tag may be linked to a bead or microsphere. Microspheres carrying a unique address tag may be uniquely labeled for easy discrimination of results. For example, each microsphere may incorporate a unique fluorescent label. Flow cytometry may be used to rapidly discriminate resuts.

Other types of specific nucleotide sequences that may be identified using the method of the invention include polynucleotide sequences, inserts, deletions, repeats, variable repeats, inversions, and the like. Applications in which the presence of an insertion or deletion is interrogated may be conducted using oligonucleotide pairs which will ligate if the insertion or deletion is present, or alternatively, using oligonucleotide pairs which will not ligate if the insertion or deletion is present. The presence, or absence, of amplicons corresponding to ligated oligonucleotide pairs provides the answer to the interrogation, depending on which approach is used.

Oligonucleotide pairs targeted to a specific sequence may be designed in a number of ways. For example, a pair may comprise one oligonucleotide which is complementary to all or part of the target sequence, the other oligonucleotide being complementary to the remaining part of the target sequence, and/or sequence adjacent to the target sequence. In another example, one oligonucleotide may have a terminus which contains the complement of the target sequence, while the other oligonucleotide contains sequence up or downstream of the target sequence. In some applications, such as the detection of larger target sequences, the oligonucleotide pair may be complementary to a region within the target sequence. In yet another example, oligonucleotide pairs may be designed such that the absence of perfect complementarity to the target sequence may nevertheless result in functional ligation between oligonucleotides under certain hybridization conditions. In such instances, it will be necessary to adjust hybridization conditions (i.e., temperature) in order to discern, preferentially, functional ligation where the target sequence is present. Many other possibilities for the design of oligonucleotides and oligonucleotide pairs will be apparent to those skilled in the art.

Multiplexed assays, capable of interrogating the state of multiple alleles on a single nucleic acid sample, may be conducted in a single reaction by combining multiple oligonucleotide pairs having intra-pair allele specificity and inter-pair common primer and primer site sequences. In multiplexed applications, a plurality of allele-specific amplicons may result from the single PCR amplification step. Accordingly, each of the possible amplicons must be distinguishable from the others. There are a variety of ways in which these resulting allele-specific amplicons may be differentiated, as discussed supra.

In one embodiment of the multiplexed assay of the invention, the presence of a plurality of specific nucleotide sequences in a sample nucleic acid is identified by first hybridizing to the sample nucleic acid a plurality of oligonucleotide pairs, wherein each oligonucleotide pair (i) targets a different specific nucleotide sequence and incorporates a means for distinguishing each from the other, (ii) ligates together when hybridized to the sample nucleic acid if the specific nucleotide sequence to which the pair is directed is present, and (iii) contains a tail sequence containing a common first PCR primer sequence on one oligonucleotide, and a tail sequence containing the complement of a common second PCR primer sequence on the other oligonucleotide. The oligonucleotides are then PCR amplified in a single reaction using the common first and second primers. The detection of target-specific amplicons, corresponding to target-specific ligated oligonucleotide pairs, is used to identify the various interrogated specific sequences.

In a specific application, different nucleic acid capture tags are incorporated into the different allele-specific oligonucleotide pairs, each of the capture tags being complementary to a nucleic acid address tag linked to a bead or microsphere, which in turn has a discriminating feature, such as a particular fluorescent label. The amplification products resulting from a multi-allele assay are then mixed with the different "allele-specific" beads or microspheres, the detection of which identifies the presence of the allele-specific amplicons. Flow cytometry may be utilized to rapidly distinguish between different microsphere-tag-amplicon complexes on the basis of the different fluorescent labels incorporated into the microspheres. Alternatively, DNA chip technologies may be utilized in the detection of different allele-specific amplicons using, for example, microarray-immobilized address nucleotide sequences capable of hybridizing their complementary capture sequences in allele-specific amplicons.

The invention further provides paired oligonucleotides comprising sequences which in tandem are complementary to a contiguous target sequence in a sample nucleic acid, one oligonucleotide further comprising a tail sequence containing a first PCR primer sequence or its complement, and the other oligonucleotide further comprising a tail sequence containing a second PCR primer sequence whenever the first oligonucleotide contains the complement of the first PCR primer sequence, or a tail sequence containing the complement of the second PCR primer sequence whenever the first oligonucleotide contains the first PCR primer sequence. The oligonucleotide pairs may further comprising a polynucleotide capture tag incorporated into at least one of the oligonucleotides.

Other applications of the method are used to identify specific nucleotide sequences corresponding to insertions, deletions, inversions, repeats, and the like.

BRIEF DESCRIPTION OF THE DRAWINGS

The accompanying drawings, which are incorporated in and form part of the specification, illustrate an embodiment of the present invention and, together with the description, serve to explain the principles of the invention. In the drawings:

FIGS. 4A and 4B schematically depict an implementation of the present invention for the scoring of single nucleotide polymorphisms.

FIGS. 5A and 5B schematically depict an implementation of the present invention for the detection of insertions or deletions.

FIGS. 6A and 6B schematically depict an implementation of the present invention for the detection of a specified number of repeat units within a specific simple repeat.

DETAILED DESCRIPTION

Figure 1:
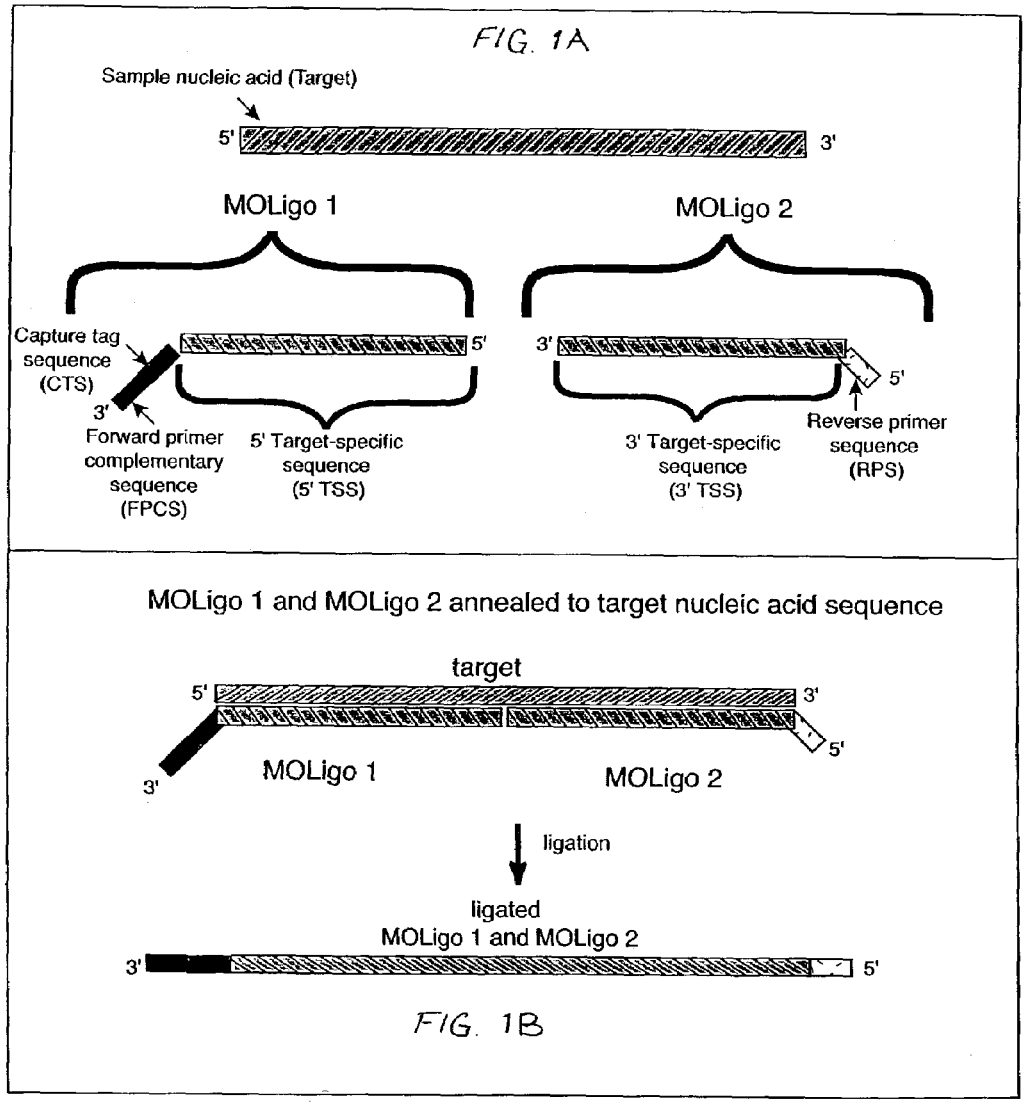
FIGS. 1A and 1B schematically depict the oligonucleotide components for multiplexed sequence detection using multiplexed oligo-ligation (MOL) PCR.

In accordance with the present invention, multiplexed oligo-ligation PCR ("MOL-PCR" herein) is accomplished by using a combination of an oligonucleotide ("oligo") ligation step, followed by multiplexed PCR amplification of all ligated oligos simultaneously. The PCR amplification is performed on the ligated oligos from all of the target nucleic acid sites at the end of the process rather than amplifying individual target sequences. Consequently only a small amount of target nucleic acid is needed and the time required assay is greatly reduced. Oligonucleotides may include complementary target sequences, PCR primer sequences, and capture tag sequences; a ligase; microspheres; and flow cytometry to determine nucleotide base composition at specific sites in a nucleic acid strand.

The multiplexed PCR step is accomplished by incorporating "tails" into the ligation oligos that serve as common priming sites for all ligation products. The use of a single primer pair for the PCR amplification step, as well as the fact that all of the ligation products would have nearly identical, short (~80–100 base pairs) lengths makes the simultaneous amplification of many, short fragments highly feasible. Hence, a plurality of target sites can be scored simultaneously. MOL-PCR also may contain in one assay design the address/tags, taught in U.S. patent application Ser. No. 09/877,819, "Address/Capture Tags for Flow-Cytometry Based Minisequencing," filed Jun. 7, 2001, incorporated herein by reference, to multiplex identification of the ligation products in the same manner as is currently used for minisequencing assays (U.S. Pat. No. 6,287,766, supra).

Full implementation of MOL-PCR will have a widespread impact on any laboratory that is performing genomic assays. MOL-PCR has properties that extend well beyond sequence detection and SNP scoring. For example, small to large insertion/deletion events (indels) are not easily scored by minisequencing or heteroduplex strategies, but MOL-PCR has inherent properties that make it ideal for these classes of DNA or RNA variants. The key property of the assay is that it requires simultaneous annealing along the lengths of two oligonucleotides in the first step, and these oligos can be designed across splice junctions, indel sites, or as part of a presence/absence screening assay designed to detect pathogens, for example.

The presently described method as applied to sequence detection and single nucleotide polymorphisms is a specific example of the analysis of a specific nucleotide base sequence feature. Other types of genetic polymorphisms, including insertion or deletions, variations in the repeated sequence, and gene rearrangements may also be scored in addition to SNPs. The applications of this methods are varied and include, but are not limited to: 1) detection of pathogenic organisms (virus, bacteria, fungi) in humans, other animals, plants, or environmental samples; 2) forensic analysis of human animal or plant material for identification purposes, the detection of genetic variation associated with disease, diseases susceptibility, or drug response.

One advantage of the present method is to allow very high factors of multiplexing in amplification of target sequence while minimizing the failure rate. By designing the tails of the ligation oligos to incorporate common primers and unique capture tags, multiple assay reactions can be performed simultaneously, i.e., multiplexed. A high degree of multiplexing will dramatically reduce the cost of screening nucleic acid samples containing a large number of SNPs whose alleles are to be scored. The present method describes a massively parallel amplification technique, termed Multiplexed Oligonucleotide Ligation PCR (MOL-PCR), which allows a more rapid sample processing without PCR amplification of the sample and a much higher degree of multiplexing than does conventional PCR. A related objective of the present method is to reduce the amplification failure rate as compared with conventional PCR, when a comparable degree of multiplexing is used.

In addition to reducing the cost of amplification through increased multiplexing, the present method increases the accuracy of the allele discrimination by shifting the discrimination from hybridization (as in some current approaches) to an enzymatic ligation step. In many current technologies, the oligonucleotides must discriminate among the two to four possible alleles. Many oligonucleotides can usually distinguish between two alternative homozygotes reasonably well. However, distinguishing between homozygous and heterozygous variants of a SNP (which is the most common scenario) often fails due to mismatched hybridization to oligonucleotides and due to other hybridization artifacts. The present method minimizes this problem by shifting the discrimination from the hybridization step to a more reliable, enzymatic discriminative step (ligation). Thus, an objective of the present method is to decrease the error rate of SNP scoring compared to some current methods.

A decreased error rate will be a significant feature for determining the presence and identity of a particular pathogen when neighbors are expected to be present in a sample. For example, if a sample is expected to contain neighbors, SNP discrimination will identify the pathogen, but will contain signal from a neighbor as well, depending upon the properties of the signature. Using MOL-PCR it is possible to detect both organisms within the sample. Additionally, the new method allows for screening for mutations in the pathogen genome, such as antibiotic resistance, where there may be a mixture of mutant and wild-type sequences present in the sample. This and other features of the current technology all emphasize the need for new assay chemistries for genotyping and detection of threat agents.

The individual components of the present invention for detecting nucleic acid sequence are depicted in FIGS. 1A and 1B. It is important to realize that in a mature assay, many different markers may be scored simultaneously, each one involving the component of a single assay from among the numerous assay types. It is also important to realize that a mature assay may comprise a mixture of assay types performed simultaneously, i.e., presence/absence detection assays, SNP scoring assays, insertion/deletion detection assays, repeat assays and inversion assays, all of which are compatible with MOL-PCR and can be performed simultaneously.

Nucleic acid sequence detection by MOL-PCR involves several steps. Once the sequences to be detected (targets) are identified, a set of oligonucleotides (MOLigos) is designed for each target. In the most general case, two MOLigos, designated MOLigo1 and MOLigo2, are designed to anneal adjacent to each other on the target sequence site of interest. In cases where the target sequence is polymorphic, such as a SNP site, and where it is desirable to identify the polymorphic variants or alleles, one or both of the MOLigos may have allele-specific sequences such that the MOL-PCR process proceeds only in the presence of the allele of interest.

For highly multiplexed reactions, the MOLigos must be appropriately designed. Primer homodimers or heterodimers have the potential to decrease the overall efficiency of the reaction or to introduce unwanted artifacts, resulting in false signals. Such undesirable interactions may be associated with the allele specific portion of the MOLigos or with the PCR primer sequence or the capture tag sequence. In many cases, computer aided oligonucleotide design can facilitate primer design by automating pairwise comparisons of the free energies of interaction for large sets of primers. While there is little flexibility in the design of the allele-specific portion of the MOLigo, as these must encompass the site of interest, sets of potential primer sequences can be analyzed to identify those that will likely produce unwanted interactions, and multiplexed primer sets can be designed that place incompatible primers in different multiplexed sets. For the PCR primer sequences and the capture tag sequences, a feasible solution is to have a large enough set of potential sequences such that a compatible sequence can always be identified for incorporation into the MOLigo.

As an example, in the case of a biallelic SNP site, two MOLigo2s can be used (MOLigo2.1 and MOLigo2.2), one each with a terminal base composed of one of two nucleotide bases complementary to the two possible bases at the SNP site on the target nucleic acid. In the case of a triallelic SNP site, three MOLigos2 can be used, bearing at the terminal base one each of three nucleotide bases complementary to the SNP site on the target nucleic acid. Similarly, for a tetraallelic site, four MOLigo2s might be used. This approach is also capable of genotyping small (~10–12 nucleotides) insertions, deletions, inversions, repeats, and variable repeats. In this case one MOLigo2 is designed for each variant, having a terminal nucleotide sequence that is complementary to one of the insert, deletion, inversion, repeat, or variable repeat variant sequences on the target nucleic acid.

Regardless of the nature of the sequence or its variation (SNP, insertion, deletion, inversion, repeat, the MOLigos will have a general set of modular components. These components and their relationship to the target nucleic acids are presented in FIG. 1, and are labeled according to the following scheme:

| Target | Sample nucleic acid |
|---|---|
| MOLigo1 | MOL-PCR oligonucleotide binding to the 5' portion of the target sequence |
| MOLigo2 | MOL-PCR oligonucleotide binding to the 3' portion of the target sequence |
| 5' TSS | Five prime target-specific sequence |
| 3' TSS | Three prime target-specific sequence |
| CTS | Capture tag sequence |
| ATS | Address tag sequence |
| FPCS | Forward primer complementary sequence |
| RPS | Reverse primer sequence |
| FP | Forward PCR primer |
| RP | Reverse PCR primer |
| ADS | Allele-defining sequence |
| ADNS | Allele-discriminating nucleotide sequence |

In FIGS. 1A and 1B, MOLigo1 is composed of the 5' SS, which is complementary to the 5' portion of the target sequence, the CTS, an optional sequence that can be used to capture amplified, ligated MOLigos onto microarrays, and the FPCS, where the forward PCR primer will bind to amplify the ligated primers. MOLigo2 is composed of the 3' TSS, which is complementary to the 3' portion of the target sequence, and the RPS, where the reverse PCR primer will bind.

Figure 2:
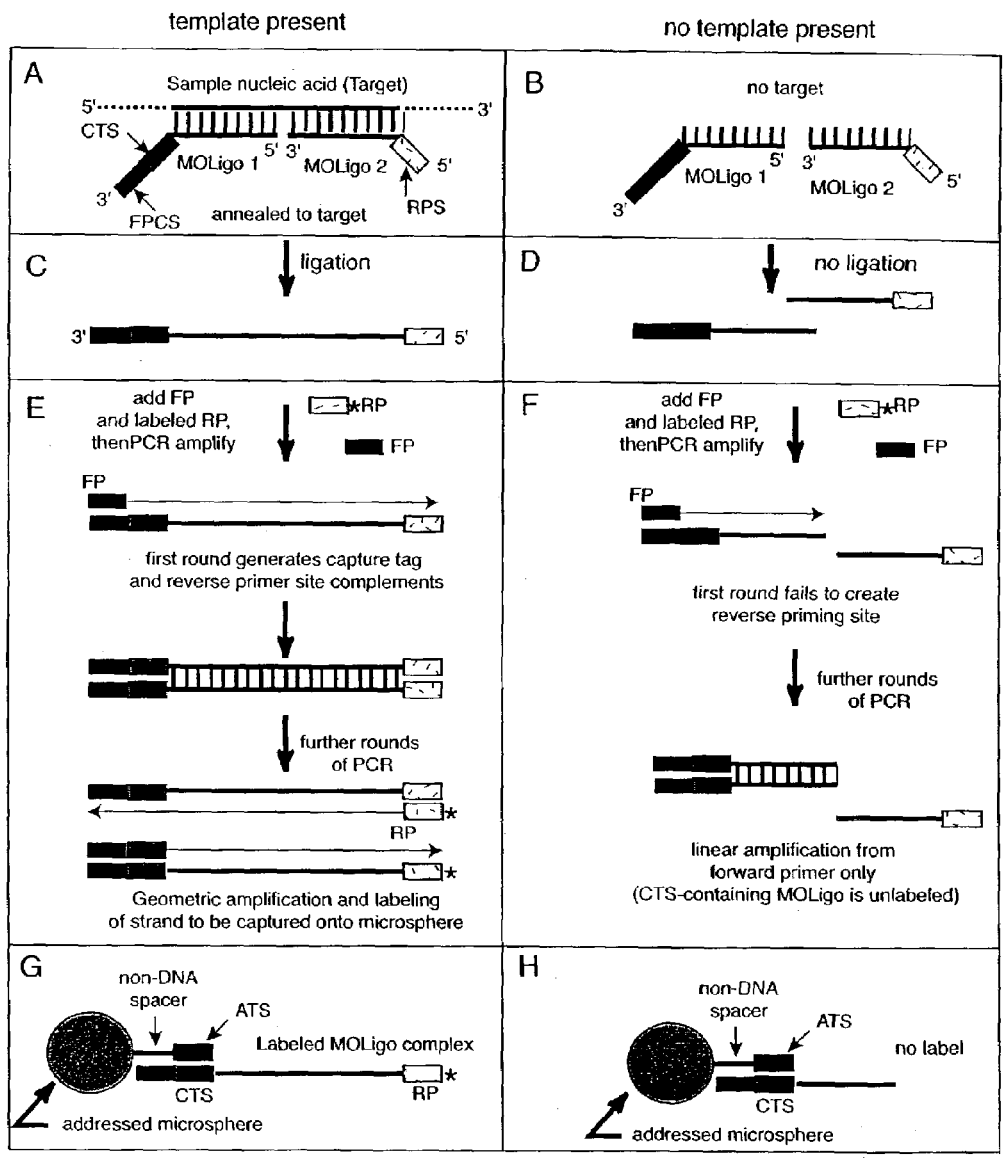
FIG. 2 schematically depicts the MOL-PCR sequence detection and amplification process of the present invention.

FIG. 2 depicts a typical MOL-PCR assay. In this example, designed to detect a target sequence, the sample is combined with a MOLigo1 and a MOLigo2. In the presence of the target, the MOLigos will anneal adjacent to each other and, upon addition of ligase enzyme, the MOLigo1 and MOLigo2 will be enzymatically ligated to form a covalently linked complex (FIG. 2, boxes A and C). In the absence of target sequence, enzymatic ligation will not occur, and no covalently linked complex will be formed (FIG. 2, box B and D).

The double stranded Target/MOLigo1–MOLigo2 complex is then denatured to separate the Target from the ligated or unligated MOLigos. Upon addition of FP and RP, the sequence newly created by the formation of the covalently linked oligonucleotide complex of MOLigo1 and MOLigo2, will be geometrically amplified by PCR (FIG. 2, box E), while in the absence of covalent ligation of MOLigo1 and MOLigo2, no geometric amplification by PCR will occur (FIG. 2, box F). After PCR amplification, the amplified MOLigo1–MOLigo2 complex can be captured onto a solid support for analysis.

The amplified MOLigo1–MOLigo2 complex can be captured via hybridization to a complex-specific sequence using an immobilized complementary oligonucleotide. Alternately, a CTS can be incorporated into one of the MOLigos and the complementary ATS can be immobilized to effect capture onto a solid support (FIG. 2, box G or box F). If either the RP or FP contain a label, this label can be used to detect the presence of the amplified MOLigo1–MOLigo2 complex captured onto the solid support. If ligation did not occur, no label is incorporated on the immobilized sequence and no signal will be present. An exemplary system of address tags for sequence identification is taught in U.S. patent application Ser. No. 09/877,819, filed Jun. 7, 2001, by White et al., incorporated herein by reference.

Figure 3:
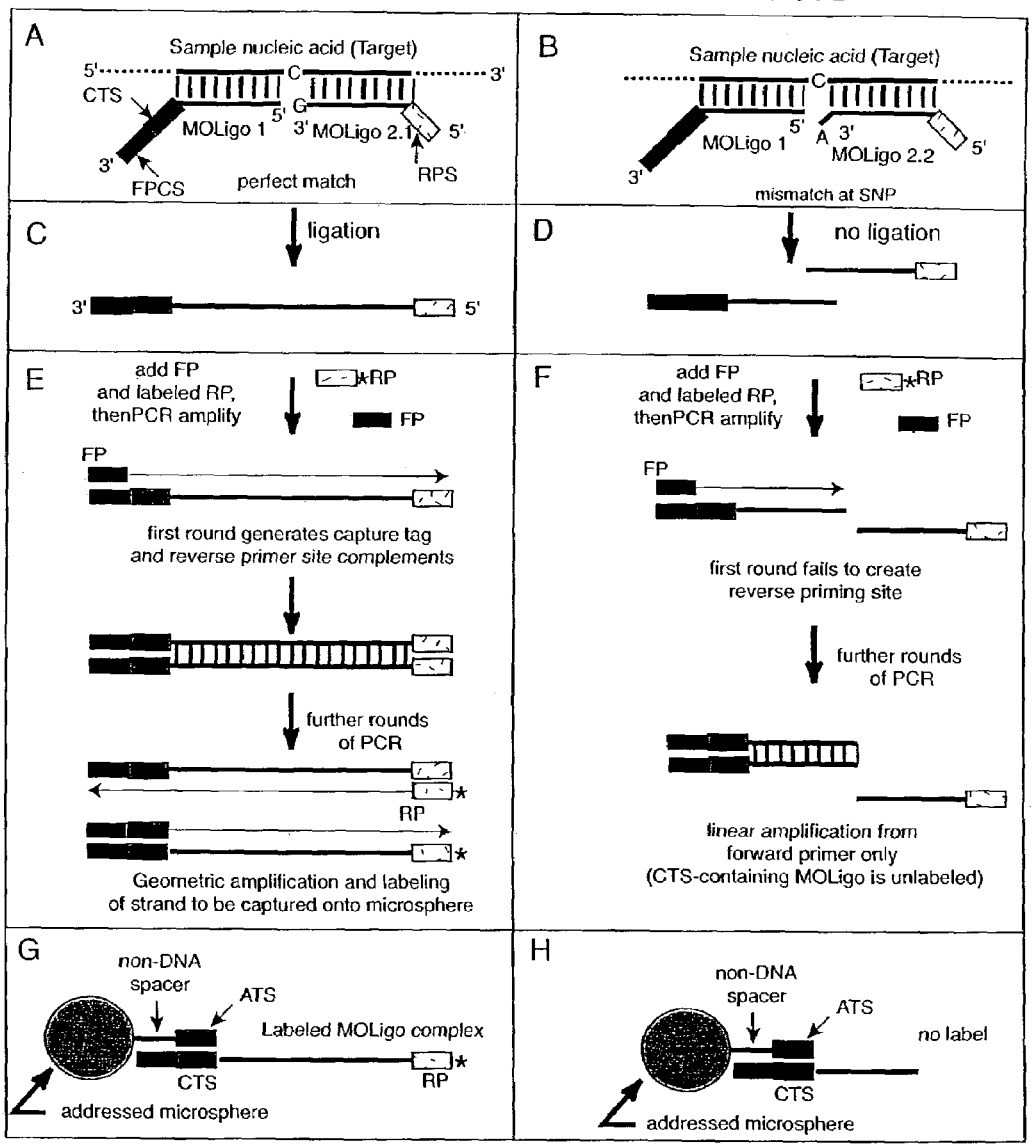
FIG. 3 schematically depicts the MOL-PCR single nucleotide polymorphism detection and amplification process of the present invention.

FIG. 3 depicts an MOL-PCR assay designed to identify SNP genotypes. In this example, designed to genotype a biallelic SNP site which may contain a C or a T, the MOLigo1 is combined with each of two MOLigo2s, in separate reactions. In one reaction, designed to detect Allele 1, the MOLigo1 is combined with MOLigo2.1, which bears an ADNS, in this case a terminal G, which is complementary to the ADS of Allele 1. In the second reaction, the MOLigo1 is combined with MOLigo2.2, which bears an ADNS, in this case an A, which is complementary to the ADS of Allele 2, but not the ADS of Allele 1. It will be recognized that the ADNS may be present at any position within the TSS such that ligation occurs only in the presence of the target sequence variant, but its presence at the terminus of MOLigo2 makes the ligation especially sensitive to the presence of the target sequence variant of interest.

In the presence of the Target, the MOLigos will anneal adjacent to each other with the ADNS opposite the ADS on the target nucleic acid strand (FIG. 3, boxes A and B). If the ADNS of MOLigo2 is complementary to the ADS, upon addition of ligase enzyme, the MOLigo1 and MOLigo2 will be enzymatically ligated to form a covalently linked complex (FIG. 3, box C). If, however, the ADNS of MOLigo2 is not complementary to the ADS of the Target, enzymatic ligation will not occur, and no covalently linked complex will be formed (FIG. 3, box D).

The double stranded Target/MOLigo1–MOLigo2.1 or Target/MOLigo1–MOLigo2.2 is then denatured to separate the Target from the ligated or unligated MOLigos. Upon addition of FP and RP, the sequence newly created by the formation of the covalently linked complex of MOLigo1 and MOLigo2.1, will be geometrically amplified by PCR (FIG. 3, box E), while in the absence of covalent ligation of MOLigo1 and MOLigo2.2 no geometric amplification by PCR will occur (FIG. 3, box F). After PCR amplification, the amplified MOLigo1–MOLigo2.1 complex can be captured onto a solid support to complete the analysis.

As with the sequence detection example depicted in FIG. 2, the amplified MOLigo1–MOLigo2.1 complex can be captured via hybridization to a complex-specific sequence using an immobilized complementary oligonucleotide. Alternately, a CTS can be incorporated into one of the MOLigos and the complementary ATS can be immobilized to effect capture onto a solid support (FIG. 3, box G or box F). If either the RP or FP contain a label, this label can be used to detect the presence of the amplified MOLigo1–MOLigo2.1 complex captured onto the solid support. If ligation did not occur, no label is incorporated on the immobilized sequence and no signal will be present.

It will be recognized that the various functional modules of the MOLigos may be combined in a number of configurations, with the ADNS, FP and RP, and CTS associated with either the 5' TSS or the 3' TSS, to enable a large number of different possible MOLigo configurations. One such configuration is described below.

Similarly, it will be recognized that the general approach described here will enable the interrogation and identification of a number of different types of nucleic acid sequence variation in addition to SNPs. For example, from the exemplary oligonucleotide configuration adapted for application to SNPs (FIGS. 4A and 4B), one can see the adaptation of the system to detect a small insertion or deletion (FIGS. 5A and 5B) wherein the ADNS is now a sequence complementary to the target sequence with or without the inserted (or deleted) sequence. Another example is the detection of a simple sequence repeat (FIGS. 6A and 6B), where the ADNS is designed to specifically detect an ADS consisting of a specific number of units of a repeated nucleotide sequence. Correspondingly, a sequence inversion would create distinct ADSs that could be detected with MOLigos bearing the appropriate ADNSs.

In another embodiment, a portion of the upstream or downstream universal segment has a sequence that is complementary to one of the tags for annealing specific MOL-PCR sequences to microspheres that, in turn, contain specific identifiers to enable the rapid discrimination of the microspheres and concomitant identification of the MOL-PCR products annealed to specific microspheres using flow cytometry. This involves (a) incorporating a polynucleotide capture tag sequence into at least one of the oligonucleotides, and (b) contacting the PCR amplification products with a microsphere linked to a polynucleotide address tag sequence complementary to the capture tag sequence, wherein the labeled amplicon is detected by optically detecting the microsphere. A suitable scheme for such tags is described in the '819 application.

It will be appreciated that any of the known high throughput sequence detection method may be used with the present invention in addition to flow cytometry. Such methods include screening on high density oligonucleotide arrays, gel electrophoresis, confocal microscopy, mass spectroscopy, and the like.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for identifying the presence of a specific nucleotide sequence in a sample nucleic acid, comprising:
 (a) hybridizing to the sample nucleic acid a pair of oligonucleotides capable of ligating together when hybridized to the sample nucleic acid if the specific nucleotide sequence is present therein, wherein one oligonucleotide further comprises a tail sequence containing a first PCR primer sequence and the other oligonucleotide further comprises a tail sequence containing the complement of a second PCR primer sequence, and wherein at least one of the oligonucleotides contains a polynucleotide capture sequence;
 (b) PCR amplifying the oligonucleotides with first and second PCR primers corresponding to the first and second PCR primer sequences, wherein at least one of the primers is labeled, to generate a PCR amplification product; and,
 (c) contacting the PCR amplification product with a microsphere linked to a polynucleotide address tag sequence complementary to the capture tag sequence, wherein the presence of the specific nucleotide sequence is identified by the detection of a labeled amplicon corresponding to a ligated oligonucleotide complex, and wherein the labeled amplicon is detected by optically detecting the microsphere.

2. A method for determining the nucleotide identity at a single nucleotide polymorphism (SNP) site in a sample nucleic acid, comprising:
 (a) hybridizing to the sample nucleic acid a plurality of oligonucleotide pairs, wherein
  (i) one or more pairs are capable of ligating together when hybridized to the sample nucleic acid if one of the nucleotides possible at the SNP site is present therein,
  (ii) each oligonucleotide pair incorporates a unique capture tag nucleotide sequence as a means for distinguishing one oligonucleotide pair from another, and
  (iii) one oligonucleotide in each pair further comprises a tail sequence containing a first PCR primer sequence and the other oligonucleotide in each pair further comprises a tail sequence containing the complement of a second PCR primer sequence;
 (b) PCR amplifying the oligonucleotides, such that an amplicon resulting from a ligated oligonucleotide pair incorporates the unique capture tag sequence as a means for distinguishing it from an amplicon resulting from a different ligated oligonucleotide pair; and,
 (c) contacting the amplicon with differentially labeled sets of microspheres, each set being linked to a polynucleotide address tag sequence uniquely complementary to one capture tag sequence,
 wherein the identity of the nucleotide at the polymorphism site is determined by detecting the presence or absence of an amplicon corresponding to a ligated oligonucleotide complex, the amplicon being detected by optically detecting the microspheres.

3. A method for identifying the presence of a specific nucleotide sequence in a sample nucleic acid, comprising:
 (a) hybridizing a pair of oligonucleotides to the sample nucleic acid in the presence of a ligase, wherein
  (i) the oligonucleotides comprise sequences which in tandem are complementary to a contiguous sequence of the sample nucleic acid spanning or including the specific nucleotide sequence,
  (ii) one oligonucleotide further comprises a tail sequence containing a first PCR primer sequence or its complement, and,
  (iii) the other oligonucleotide further comprises a tail sequence containing a second PCR primer sequence whenever the first oligonucleotide contains the complement of the first PCR primer sequence, or a tail sequence containing the complement of the second PCR primer sequence whenever the first oligonucleotide contains the first PCR primer sequence, and wherein at least one of the oligonucleotides contains a polynucleotide capture sequence, under conditions permitting the ligation of the two oligonucleotides if the specific nucleotide sequence is present in the sample nucleic acid;
 (b) PCR amplifying the oligonucleotides using first and second PCR primers corresponding to the first and second PCR primer sequences, wherein at least one of the primers is labeled, to generate a PCR amplification product; and,
 (c) contacting the PCR amplification products with a microsphere linked to a polynucleotide address tag sequence complementary to the capture tag sequence, wherein the presence of the specific nucleotide sequence is identified by the detection of a labeled amplicon corresponding to a ligated oligonucleotide complex, and wherein the labeled amplicon is detected by optically detecting the microsphere.

4. A method for determining the nucleotide identity at a single nucleotide polymorphism (SNP) site in a sample nucleic acid, comprising:
 (a) hybridizing one or more pairs of oligonucleotides to the sample nucleic acid in the presence of a ligase, wherein
  (i) for each specific nucleotide possible at the single nucleotide polymorphism site is provided an oligonucleotide pair comprising sequences which in tandem would be complementary to a contiguous sequence of the sample nucleic acid including the single nucleotide polymorphism site, (ii) one oligonucleotide in each pair further comprises a tail sequence containing a first PCR primer sequence or its complement, (iii) the other oligonucleotide in each pair further comprises a tail sequence containing a second PCR primer sequence whenever the other oligonucleotide in the pair contains the complement of the first PCR primer sequence, or a tail sequence containing the complement of the second PCR primer sequence whenever the other oligonucleotide in the pair contains the first PCR primer sequence, and (iv) where a plurality of oligonucleotide pairs is hybridized, each oligonucleotide pair incorporates a different capture tag nucleotide sequence as means for distinguishing each from the other, under conditions permitting the ligation of oligonucleotide pairs which in tandem are complementary to a contiguous sequence of the sample nucleic acid including one of the specific nucleotides at the single nucleotide polymorphism site;

(b) PCR amplifying the oligonucleotides to generate a PCR amplification product, using first and second PCR primers corresponding to the first and second PCR primer sequences, such that an amplicon resulting from a ligated oligonucleotide pair incorporates the unique capture tag sequence as a means for distinguishing it from an amplicon resulting from a different ligated oligonucleotide pair; and, (c) contacting the PCR amplification products with differentially labeled sets of microspheres, each set being linked to a polynucleotide address tag sequence uniquely complementary to one capture tag sequence, wherein the identity of the base at the polymorphism site is determined by detecting the presence or absence of an amplicon corresponding to a ligated oligonucleotide complex, the amplicon being detected by optically detecting the microspheres.

5. A method for identifying the presence of a plurality of specific nucleotide sequences in a sample nucleic acid, comprising:

(a) hybridizing a plurality of oligonucleotide pairs to the sample nucleic acid in the presence of a ligase, wherein each oligonucleotide pair (i) consists of two oligonucleotides comprising sequences which in tandem are complementary to a contiguous sequence of the sample nucleic acid spanning or including one of the specific nucleotide sequences, (ii) incorporates a unique capture tag nucleotide sequence as a means for distinguishing one oligonucleotide pair from another: and, (ii) incorporates a tail sequence containing a common first PCR primer sequence in one oligonucleotide, and a tail sequence containing the complement of a common second PCR primer sequence in the other oligonucleotide, under conditions permitting the ligation of an oligonucleotide pair when hybridized to the sample nucleic acid if the specific nucleotide sequence to which the pair is complementary is present, (b) PCR amplifying the oligonucleotides using common first and second primers in a single reaction; and, (c) contacting resulting PCR amplification products with differentially labeled sets of microspheres, each set being linked to a polynucleotide address tag sequence uniquely complementary to one capture tag sequence, the presence of each specific nucleotide sequence being identified by the detection of an amplicon corresponding to the ligated oligonucleotide pair complementary to that specific nucleotide sequence, wherein an amplicon is detected by optically detecting the microsphere.

* * * * *

SEQUENCE LISTING

<160> NUMBER OF SEQ ID NOS: 23

<210> SEQ ID NO 1
<211> LENGTH: 48
<212> TYPE: DNA
<213> ORGANISM: Artificial Sequence
<220> FEATURE:
<223> OTHER INFORMATION: sequence for illustsration
<220> FEATURE:
<221> NAME/KEY: misc_feature
<222> LOCATION: (1)..(3)
<223> OTHER INFORMATION: n is a, c, g, t or u
<220> FEATURE:
<221> NAME/KEY: misc_feature
<222> LOCATION: (45)..(48)
<223> OTHER INFORMATION: n is a, c, g, t or u

<400> SEQUENCE: 1
nnnttctaag actcactgga ctatcttatg gtagcgttaa tctcnnnn        48

<210> SEQ ID NO 2
<211> LENGTH: 41
<212> TYPE: DNA
<213> ORGANISM: Artificial Sequence
<220> FEATURE:
<223> OTHER INFORMATION: sequence for illustsration

<400> SEQUENCE: 2
aagattctga gtgacctgat agaataccat cgcaattaga g        41

<210> SEQ ID NO 3
<211> LENGTH: 41
<212> TYPE: DNA
<213> ORGANISM: Artificial Sequence
<220> FEATURE:
<223> OTHER INFORMATION: sequence for illustsration

<400> SEQUENCE: 3
aagattctga gtgacctgat agaataccat cgcaattaga g        41

<210> SEQ ID NO 4
<211> LENGTH: 48
<212> TYPE: DNA
<213> ORGANISM: Artificial Sequence
<220> FEATURE:
<223> OTHER INFORMATION: sequence for illustsration
<220> FEATURE:
<221> NAME/KEY: misc_feature
<222> LOCATION: (1)..(3)
<223> OTHER INFORMATION: n is a, c, g, t or u
<220> FEATURE:
<221> NAME/KEY: misc_feature
<222> LOCATION: (45)..(48)
<223> OTHER INFORMATION: n is a, c, g, t or u

<400> SEQUENCE: 4
nnnttctaag actcactgga ctatcttatg gtagcgttaa tctcnnnn        48

<210> SEQ ID NO 5
<211> LENGTH: 41
<212> TYPE: DNA
<213> ORGANISM: Artificial Sequence
<220> FEATURE:
<223> OTHER INFORMATION: sequence for illustsration

<400> SEQUENCE: 5
aagattctga gtgacctgat aaaataccat cgcaattaga g        41

```
<210> SEQ ID NO 6
<211> LENGTH: 21
<212> TYPE: DNA
<213> ORGANISM: Artificial Sequence
<220> FEATURE:
<223> OTHER INFORMATION: sequence for illustsration

<400> SEQUENCE: 6
aagattctga gtgacctgat a                                              21

<210> SEQ ID NO 7
<211> LENGTH: 20
<212> TYPE: DNA
<213> ORGANISM: Artificial Sequence
<220> FEATURE:
<223> OTHER INFORMATION: sequence for illustsration

<400> SEQUENCE: 7
aaataccatc gcaattagag                                                20

<210> SEQ ID NO 8
<211> LENGTH: 48
<212> TYPE: DNA
<213> ORGANISM: Artificial Sequence
<220> FEATURE:
<223> OTHER INFORMATION: sequence for illustsration
<220> FEATURE:
<221> NAME/KEY: misc_feature
<222> LOCATION: (1)..(3)
<223> OTHER INFORMATION: n is a, c, g, t or u
<220> FEATURE:
<221> NAME/KEY: misc_feature
<222> LOCATION: (45)..(48)
<223> OTHER INFORMATION: n is a, c, g, t or u

<400> SEQUENCE: 8
nnnttctaag actcactgga ctatcttatg gtagcgttaa tctcnnnn                 48

<210> SEQ ID NO 9
<211> LENGTH: 41
<212> TYPE: DNA
<213> ORGANISM: Artificial Sequence
<220> FEATURE:
<223> OTHER INFORMATION: sequence for illustsration

<400> SEQUENCE: 9
aagattctga gtgacctgat agaataccat cgcaattaga g                        41

<210> SEQ ID NO 10
<211> LENGTH: 41
<212> TYPE: DNA
<213> ORGANISM: Artificial Sequence
<220> FEATURE:
<223> OTHER INFORMATION: sequence for illustsration

<400> SEQUENCE: 10
aagattctga gtgacctgat agaataccat cgcaattaga g                        41

<210> SEQ ID NO 11
<211> LENGTH: 57
<212> TYPE: DNA
<213> ORGANISM: Artificial Sequence
<220> FEATURE:
<223> OTHER INFORMATION: sequence for illustsration
<220> FEATURE:
<221> NAME/KEY: misc_feature
<222> LOCATION: (1)..(3)
```

```
<223> OTHER INFORMATION: n is a, c, g, t or u
<220> FEATURE:
<221> NAME/KEY: misc_feature
<222> LOCATION: (54)..(57)
<223> OTHER INFORMATION: n is a, c, g, t or u

<400> SEQUENCE: 11
nnnttctaag actcactgga ctatggatac ctgcttatgg tagcgttaat ctcnnnn        57

<210> SEQ ID NO 12
<211> LENGTH: 21
<212> TYPE: DNA
<213> ORGANISM: Artificial Sequence
<220> FEATURE:
<223> OTHER INFORMATION: sequence for illustsration

<400> SEQUENCE: 12
aagattctga gtgacctgat a                                               21

<210> SEQ ID NO 13
<211> LENGTH: 20
<212> TYPE: DNA
<213> ORGANISM: Artificial Sequence
<220> FEATURE:
<223> OTHER INFORMATION: sequence for illustsration

<400> SEQUENCE: 13
gaataccatc gcaattagag                                                 20

<210> SEQ ID NO 14
<211> LENGTH: 21
<212> TYPE: DNA
<213> ORGANISM: Artificial Sequence
<220> FEATURE:
<223> OTHER INFORMATION: sequence for illustsration

<400> SEQUENCE: 14
aagattctga gtgacctgat a                                               21

<210> SEQ ID NO 15
<211> LENGTH: 20
<212> TYPE: DNA
<213> ORGANISM: Artificial Sequence
<220> FEATURE:
<223> OTHER INFORMATION: sequence for illustsration

<400> SEQUENCE: 15
gaataccatc gcaattagag                                                 20

<210> SEQ ID NO 16
<211> LENGTH: 53
<212> TYPE: DNA
<213> ORGANISM: Artificial Sequence
<220> FEATURE:
<223> OTHER INFORMATION: sequence for illustsration
<220> FEATURE:
<221> NAME/KEY: misc_feature
<222> LOCATION: (1)..(3)
<223> OTHER INFORMATION: n is a, c, g, t or u
<220> FEATURE:
<221> NAME/KEY: misc_feature
<222> LOCATION: (50)..(53)
<223> OTHER INFORMATION: n is a, c, g, t or u

<400> SEQUENCE: 16
nnnttctaag actcactgga ctataactct ctctggtagc gttaatctcn nnn             53
```

```
<210> SEQ ID NO 17
<211> LENGTH: 46
<212> TYPE: DNA
<213> ORGANISM: Artificial Sequence
<220> FEATURE:
<223> OTHER INFORMATION: sequence for illustsration

<400> SEQUENCE: 17
aagattctga gtgacctgat attgagagag accatcgcaa ttagag              46

<210> SEQ ID NO 18
<211> LENGTH: 49
<212> TYPE: DNA
<213> ORGANISM: Artificial Sequence
<220> FEATURE:
<223> OTHER INFORMATION: sequence for illustsration

<400> SEQUENCE: 18
aagattctga gtgacctgat attgagagag aataccatcg caattagag            49

<210> SEQ ID NO 19
<211> LENGTH: 57
<212> TYPE: DNA
<213> ORGANISM: Artificial Sequence
<220> FEATURE:
<223> OTHER INFORMATION: sequence for illustsration
<220> FEATURE:
<221> NAME/KEY: misc_feature
<222> LOCATION: (1)..(3)
<223> OTHER INFORMATION: n is a, c, g, t or u
<220> FEATURE:
<221> NAME/KEY: misc_feature
<222> LOCATION: (54)..(57)
<223> OTHER INFORMATION: n is a, c, g, t or u

<400> SEQUENCE: 19
nnnttctaag actcactgga ctataactct ctctctctgg tagcgttaat ctcnnnn    57

<210> SEQ ID NO 20
<211> LENGTH: 21
<212> TYPE: DNA
<213> ORGANISM: Artificial Sequence
<220> FEATURE:
<223> OTHER INFORMATION: sequence for illustsration

<400> SEQUENCE: 20
aagattctga gtgacctgat a                                           21

<210> SEQ ID NO 21
<211> LENGTH: 25
<212> TYPE: DNA
<213> ORGANISM: Artificial Sequence
<220> FEATURE:
<223> OTHER INFORMATION: sequence for illustsration

<400> SEQUENCE: 21
ttgagagaga ccatcgcaat tagag                                       25

<210> SEQ ID NO 22
<211> LENGTH: 21
<212> TYPE: DNA
<213> ORGANISM: Artificial Sequence
<220> FEATURE:
<223> OTHER INFORMATION: sequence for illustsration

<400> SEQUENCE: 22
aagattctga gtgacctgat a                                           21
```

```
<210> SEQ ID NO 23
<211> LENGTH: 25
<212> TYPE: DNA
<213> ORGANISM: Artificial Sequence
<220> FEATURE:
<223> OTHER INFORMATION: sequence for illustration

<400> SEQUENCE: 23
ttgagagaga ccatcgcaat tagag                                           25
```